US00PP25472P2

(12) United States Plant Patent
Zampini

(10) Patent No.: US PP25,472 P2
(45) Date of Patent: Apr. 28, 2015

(54) ***LONICERA* PLANT NAMED 'LILEZEZAM'**

(50) Latin Name: *Lonicera nitida*
Varietal Denomination: Lilezezam

(71) Applicant: James W. Zampini, Fairport Harbor, OH (US)

(72) Inventor: James W. Zampini, Fairport Harbor, OH (US)

(73) Assignee: Lake Country Nursery, Perry, OH (US)

( * ) Notice: Subject to any disclaimer, the term of this patent is extended or adjusted under 35 U.S.C. 154(b) by 111 days.

(21) Appl. No.: 13/815,620

(22) Filed: Mar. 13, 2013

(51) Int. Cl.
*A01H 5/00* (2006.01)
*A01H 5/02* (2006.01)

(52) U.S. Cl.
CPC ..... *A01H 5/02* (2013.01)
USPC ..... Plt./226

(58) Field of Classification Search
CPC ..... A01H 5/02; A01H 5/00; A01H 5/12; A01H 5/025
USPC ..... Plt./226
See application file for complete search history.

(56) References Cited

PUBLICATIONS

Kimberley. Horticulture Week Feb. 12, 2010, retrieved on Aug. 28, 2014, retrieved from the Internet at <http://www.hortweek.com/shrubby-lonicera/article/982820> 7 pp.*

* cited by examiner

*Primary Examiner* — June Hwu
(74) *Attorney, Agent, or Firm* — Penny J. Aguirre

(57) ABSTRACT

A new cultivar of *Lonicera*, 'Lilezezam', that is characterized by its variegated foliage with green centers and yellow-green margins, its evergreen to semi-evergreen foliage depending on growing location, its yellowish white flowers, its exhibits an upright and spreading plant habit, its upright and spreading plant habit, its blue fruit and its moderate growth habit.

2 Drawing Sheets

Botanical classification: *Lonicera nitida.*
Variety denomination: 'Lilezezam'.

BACKGROUND OF THE INVENTION

The present invention relates to a new and distinct cultivar of *Lonicera nitida*, and will be referred to hereafter by its cultivar name, 'Lilezezam'. 'Lilezezam' is a new cultivar of box honeysuckle, a shrub grown for use as an ornamental landscape plant.

The Inventor discovered the new cultivar in summer of 2009 as a naturally occurring branch mutation of an unnamed plant of *Lonicera nitida* that was growing in a container block at his nursery in Perry, Ohio.

Asexual propagation of the new cultivar was first accomplished by the Inventor using stem cuttings in summer of 2009 in Perry, Ohio. Asexual propagation of the new cultivar by stem cuttings has been determined that the characteristics are stable and are reproduced true to type in successive generations.

SUMMARY OF THE INVENTION

The following traits have been repeatedly observed and represent the characteristics of the new cultivar as grown outdoors in a trial plot in Perry, Ohio. These attributes in combination distinguish 'Lilezezam' as unique cultivar of *Lonicera.*

1. 'Lilezezam' exhibits variegated foliage with green centers and yellow-green margins.
2. 'Lilezezam' exhibits evergreen to semi-evergreen foliage depending on growing location.

3. 'Lilezezam' exhibits an upright and spreading plant habit.
4. 'Lilezezam' exhibits a moderate growth habit.

The parent plant of 'Lilezezam' differs from 'Lilezezam' in having dark green non-variegated foliage. 'Lilezezam' can be most closely compared to the cultivars 'Variegata', 'Pat's Variegated', and 'Lemon Beauty' (all not patented). All are similar to 'Lilezezam' in having variegated foliage. 'Variegate' and 'Pat's Variegated' both differ from 'Lilezezam' in having leaves with margins that are creamy white in color. 'Lemon Beauty' differs from 'Lilezezam' in having leaf margins that emerge yellow-green but are less vivid and turn creamy white as they mature.

BRIEF DESCRIPTION OF THE DRAWINGS

The accompanying colored photographs were taken in mid summer and illustrate the overall appearance and distinct characteristics of 2 year-old plants the new *Lonicera* as grown in a 3-gallon container in Perry, Ohio.

The photograph in FIG. 1 provides an overall view of 'Lilezezam'.

Figure 1:
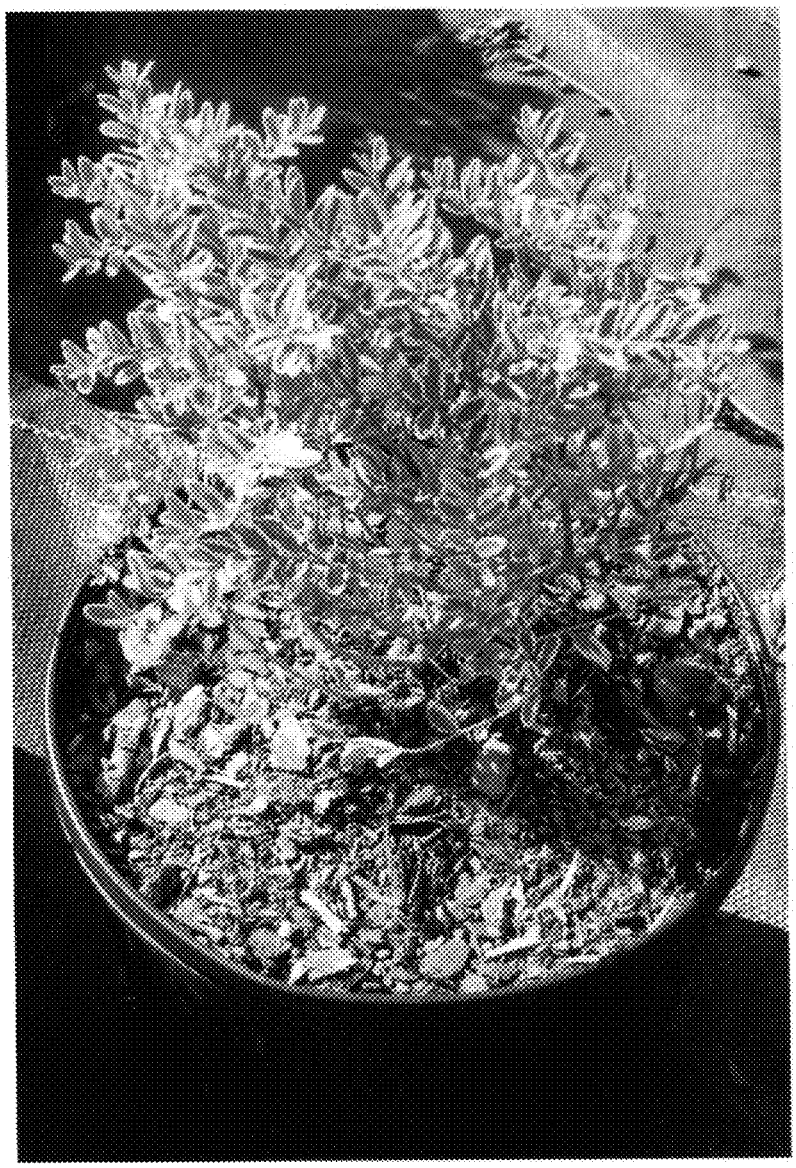
Figure 2:
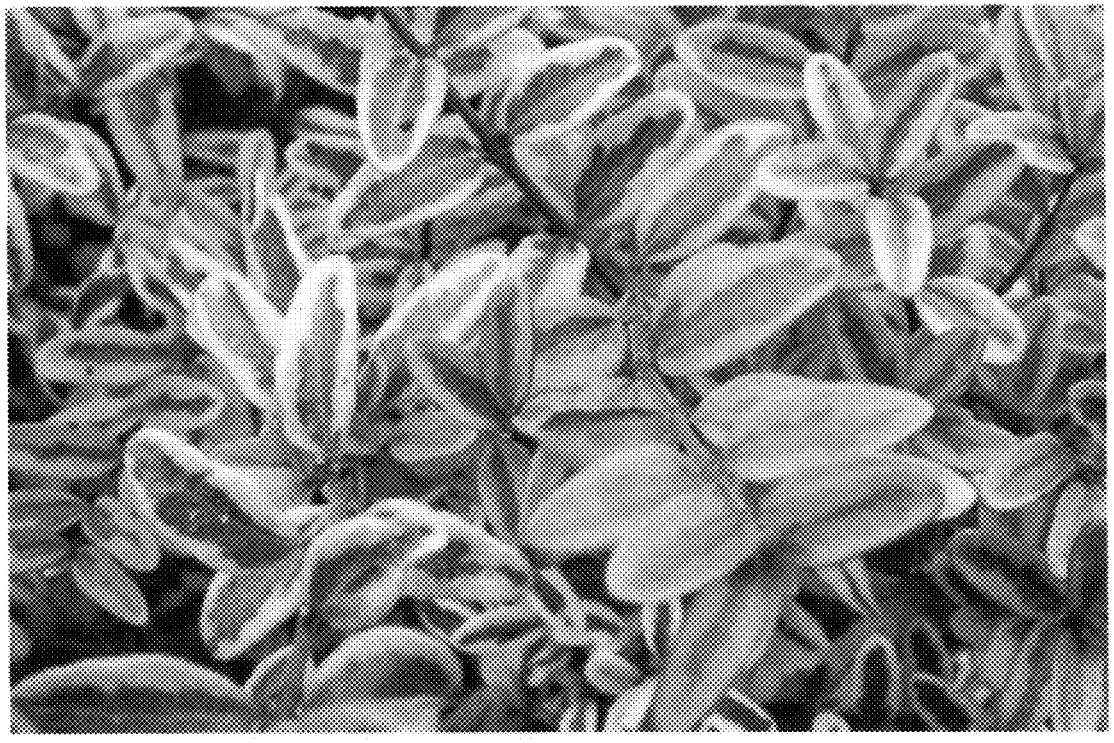

The photograph in FIG. 2 provides a close-up view of the foliage of 'Lilezezam' in spring.

Figure 3:
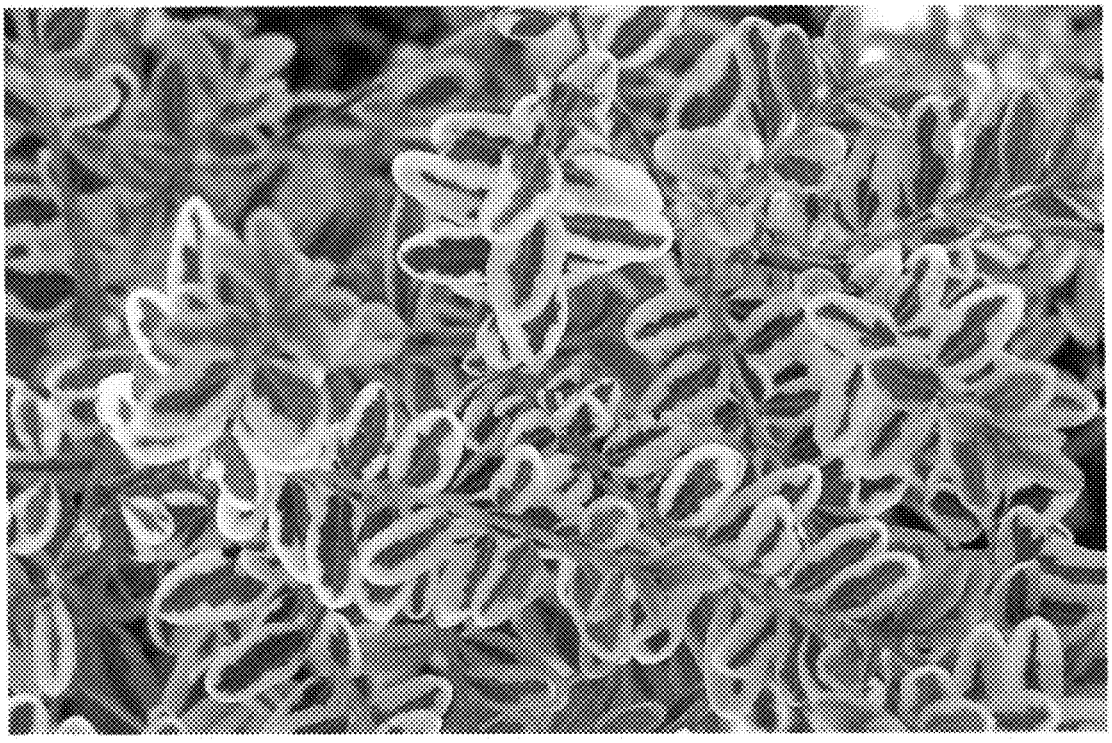

The photograph in FIG. 3 provides a close-up view of the foliage of 'Lilezezam' in late summer.

The colors in the photographs may differ slightly from the color values cited in the detailed botanical description, which accurately describe the colors of the new *Lonicera.*

DETAILED BOTANICAL DESCRIPTION

The following is a detailed description of 3 year-old plants the new *Lonicera* as grown in 3-gallon containers in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Shrub; evergreen to semi-evergreen depending on growing location.

*Plant habit*.—Upright and spreading.

*Plant height and spread*.—Reaches 76 to 91 cm in height and spread as a three year-old plant.

*Diseases and pests*.—The new cultivar has been observed to be disease free to date under the conditions of trials.

*Root description*.—Fibrous.

*Propagation*.—Softwood stem cuttings, under mist in summer.

*Growth rate*.—Moderate.

Stem description:

*Shape*.—Oval.

*Stem color*.—New growth upper surface; 144C with areas of 59B lower surface; 144C, mature wood; 199C, maturing to bark 199C in color.

*Stem size*.—Old wood; ranges about 1.2 cm in diameter near base to 3.5 mm in diameter and 35 cm in length on lateral branches, new growth; average of 0.8 mm in diameter and 10 cm in length.

*Stem surface*.—New growth; very slightly pubescent, mature wood is dull and smooth and becoming bark-like as it ages.

*Internode length*.—New growth 5.5 mm; mature stem, 11.5 mm.

*Branching*.—One main branch with an average of 5 lateral branches.

Foliage description:

*Leaf shape*.—Elliptic to oblong.

*Leaf division*.—Simple.

*Leaf base*.—Cuneate.

*Leaf apex*.—Rounded to slightly acute.

*Leaf fragrance*.—None.

*Leaf venation*.—Pinnate, only mid rib is somewhat conspicuous, color on upper and lower surfaces; 144C.

*Leaf margins*.—Entire.

*Leaf arrangement*.—Opposite.

*Leaf attachment*.—Petiolate.

*Leaf surface*.—Glabrous and slightly glossy on upper surface and lower surface.

*Leaf size*.—Average of 19 cm in length and 6.5 cm in width.

*Leaf quantity*.—Average of 20 pair per branch 35 cm in length.

*Leaf variegation pattern*.—Green 139A centers and yellow-green ranging between N144A and 144B margins.

*Leaf color*.—Newly expanded leaves upper surface; 144A, newly expanded leaves lower surface; 144C, mature leaves upper surface; centers 139A, margins a color between N144A and 144B to slightly lighter mature leaves lower surface; centers 144A, margins a color between N144A and 144B to slightly lighter, fall color upper surface; centers N137A, margins 162C, fall color lower surface; centers 138B, margins 162D.

*Petioles*.—About 0.9 mm in length and 0.7 mm in width, 144C in color, glabrous surface.

*Stipules*.—About 1.0 mm in length and 0.9 mm in width, apex, split in two, acute and 59C in color, base; a blend of 144C and 59B.

Inflorescence description: Flowering and fruit production has not been observed to date.

It is claimed:

1. A new and distinct cultivar of *Lonicera* plant named 'Lilezezam' as herein illustrated and described.

* * * * *